United States Patent [19]

DelliColli et al.

[11] 4,244,728
[45] Jan. 13, 1981

[54] CROSS-LINKED LIGNIN GELS

[75] Inventors: Humbert T. DelliColli; Peter Dilling, both of Charleston; Sten I. Falkehag, Mt. Pleasant, all of S.C.

[73] Assignee: Westvaco Corporation, New York, N.Y.

[21] Appl. No.: 654,884

[22] Filed: Feb. 3, 1976

[51] Int. Cl.³ ............................................. A01N 25/04
[52] U.S. Cl. .......................................... 71/65; 71/79; 71/115; 71/116; 71/117; 71/DIG. 1
[58] Field of Search ............... 260/124 R; 71/DIG. 1, 71/79, 117, 65; 424/22

[56] References Cited

U.S. PATENT DOCUMENTS

| | | | |
|---|---|---|---|
| 3,223,513 | 12/1965 | Geary | 71/117 |
| 3,235,366 | 2/1966 | Seymour et al. | 71/117 |
| 3,470,148 | 9/1969 | Allan | 71/DIG. 1 |
| 3,551,556 | 12/1970 | Kliment et al. | 424/22 |
| 3,759,826 | 9/1973 | Felicetta et al. | 260/124 R |
| 3,813,236 | 5/1974 | Allan | 71/DIG. 1 |
| 3,886,101 | 5/1975 | Felicetta et al. | 260/124 R |
| 3,900,378 | 8/1975 | Yen et al. | 71/DIG. 1 |
| 3,912,706 | 10/1975 | Rachor et al. | 260/124 R |
| 3,929,453 | 12/1975 | Dimitri et al. | 71/118 |

*Primary Examiner*—Glennon H. Hollrah
*Attorney, Agent, or Firm*—Richard L. Schmalz; Ernest B. Lipscomb, III; Terry B. McDaniel

[57] ABSTRACT

Disclosed herein are cross-linked lignin gels which have been found useful as pesticide carriers in controlled release pesticide systems. The carrier is a highly reswellable cross-linked lignin gel prepared by reacting alkali lignin with from 1 mole to 10 moles of cross-linking agent, such as formaldehyde, per 1,000 grams of lignin. An aqueous solution of lignin and the cross-linking agent is reacted at elevated temperatures until cross-linking occurs to the point where a discernible increase in viscosity takes place and the gel is formed. The gels are allowed to dehydrate, and the pesticide in an amount from 0.1:1.0 to 2:1 (pesticide to carrier) is included by reswelling the dehydrated gel in an aqueous solution of the pesticide.

5 Claims, No Drawings

CROSS-LINKED LIGNIN GELS

BACKGROUND OF THE INVENTION

(1) Field of the Invention

This invention relates to cross-linked lignin gels and processes for making same. More particularly, this invention relates to improved lignin-based carrier useful for the sustained release of pesticides.

The effectiveness of pesticides is controlled by the amounts of toxicity, chemical degradation, biological degradation, run-off, leaching and evaporation.

The reduction of losses of pesticides can be accomplished in developing pesticides insensitive to the chemical, physical and biological means of reducing their effectiveness. Another is the development of delivery systems which protect the pesticide from degradation and limit its availability to leaching, run-off and volatilization, while releasing the pesticide at a rate sufficient for effective biological control. In this later method the pesticide is placed in a matrix which has both the chemical and physical properties necessary to inhibit the undesirable pathways of agent removal. Controlled release thus extends control to both the length and the degree of availability of biologically active material. This is in contrast to the older, slow release systems, which are systems containing several times the normal single dose of active ingredient and which provide for replacement of agents at a rate giving meritable increases in the length of time of activity.

(2) The Prior Art

One method of controlling the release of pesticides using a lignin polymer is provided in U.S. Pat. No. 3,813,236 to G. G. Allan. The Allan patent discloses chemical co-valent bonding of a pesticide to a lignin polymeric substrate. The pesticide is released by destruction of co-valent chemical bonds.

Another example of using lignin for controlling the release of pesticides is disclosed in U.S. Pat. No. 3,929,453 to Dimitri and Falkehag. Dimitri and Falkehag disclose physical bonding of a lignin polymer and pesticide.

Although it is known to form controlled release systems based on alkali lignins, it is the purpose of this invention to provide an improved lignin matrix for this purpose in which a gel is formed by cross-linking the lignin molecules with formaldehyde glyoxal, glutaric dialdehyde or combinations of epichlorohydrin and the difunctional aldehydes in such a manner as to form a reswellable gel. For the purpose of this invention, a lignin gel shall mean a three-dimensional physically or chemically cross-linked matrix which can be repeatedly dehydrated and reswollen to its original volume.

The cross-linked lignin gels of this invention are used to produce sustained release compositions by physically mixing organic pesticides with an improved carrier comprising a cross-linked, reswellable lignin gel. It is, therefore, the general object of this invention to provide cross-linked lignin gel for use in a sustained release composition having a pesticide interspersed and physically bound throughout the cross-linked, reswellable alkali lignin gel.

Another object of this invention is to provide processes for producing the cross-linked gel and for interspersing a pesticide throughout the gel by physical contact forming a composite.

It is a specific object of this invention to provide a controlled release pesticide system comprising as a composite, a pesticide interspersed throughout an alkali lignin-formaldehyde cross-linked matrix whereby the release rate of the pesticide is accomplished through the diffusion of the pesticide through the alkali lignin matrix or through degradation or dissolution of the lignin matrix or a combination of both.

Other objects, features and advantages of this invention will become evident from the foregoing detailed description.

SUMMARY OF THE INVENTION

The lignin gels of this invention are prepared by reacting an aqueous solution of alkali lignin with from 1 mole to 10 moles of cross-linking agent per 1,000 grams of lignin at a temperature between 10° C. to 100° C. until cross-linking occurs to the point where a discernible increase in viscosity takes place and a gel is formed. Upon drying, the cross-linked lignin gel is dehydrated. To this dehydrated gel is mixed a water-soluble organic pesticide. Water-insoluble pesticides may be used if first dissolved in a water-miscible solvent. When the pesticide and lignin gel are mixed together, the pesticide is included in the gel as it reswells. The composite is then dried, crushed and screened to the proper size of materials. The weight of pesticide to carrier should be from 0.1:1.0 to 2:1.

DETAILED DESCRIPTION OF THE INVENTION

It has thus been found that controlled release properties may be obtained from the physical incorporation of a pesticide into a lignin gel by utilizing the improved lignin gel of this invention.

The desirability of an alkali lignin as carrier in controlled release systems is supported by several facts. Perhaps, the most attractive property of alkali lignin is its chemical uniqueness. The functionality of lignin consisting of phenolic hydroxyl, carboxylate, aliphatic hydroxyl groups, as well as, the higher aromatic content of the branch work comprising the lignin unit or molecule allows it to be modified. For example, cross-linking the molecule can produce a three-dimensional matrix. Cross-linking can block polar functional groups or form C—C bonds between positions adjacent to the phenolic hydroxyls creating networks varying in pore structure and polarity. Chemical modification of the lignin can also produce gels held together by secondary forces, such as hydrogen bonding and Van der Waal's forces. Once modified, the lignin can take the form of fine powders or coarse granules. Here the changes are purely physical and largely controlled by factors, such as drying conditions and means of grinding or milling.

The high aromatic content of lignin makes it an excellent ultraviolet radiation absorber. This is particularly important since many non-persistent pesticide and insect growth regulators are sensitive to UV catalyzed hydrolysis or other degrading processes. Such a process generally renders the pesticide biologically inactive. The antioxidant properties of lignin add further stability to materials incorporated into a lignin matrix.

Any of the alkali lignins may be employed to make the carrier used in this invention. These lignins are derived by the alkaline digestion of lignocellulosic material. Most commonly, they are obtained as byproducts from the alkaline process of papermaking where sodium hydroxide alone or in combination with sodium sulfide is employed. These lignins are generally referred to as soda and kraft or sulfate lignins after the pulping process used. Such alkali lignin starting material is employed in the salt form, i.e., where the sodium or potassium cation has replaced the hydrogen, so it will be water soluble. Additionally, other water soluble, salt-forming cations may be used, such as ammonia. In the preferred practice of this invention, the alkali lignin employed is a kraft pine lignin. Likewise, lignins known as "hydrolysis lignins" obtained by enzymatic or acidic reactions with lignocellulosic materials may be used. Also, sulfite waste liquor lignins and sulfonated alkali lignins may be used if the degree of sulfonation is kept low. Thus, mixtures of alkali lignin and sulfite or sulfonated lignin may be used if an immediate release of pesticide is desired.

Preparing the Carrier

The improved carrier is a gel which by I.U.P.A.C. definition means that it is reversibly swellable. The carrier is made by reacting a salt of a lignin which has been dissolved in a solution of from 10% to 40% weight by volume of the lignin into water, preferably 20% to 25%. Although the pH of the cross-linking reaction is not a critical factor, the most desirable swelling characteristics are obtained when the reactions are carried out at about pH 12.

To the aqueous lignin solution is added the cross-linking agent in an amount of 1 to 10 moles of formaldehyde per 1,000 grams of lignin. The cross-linking agent may be formaldehyde or a formaldehyde-forming material, such as paraformaldehyde, glyoxal, glutaric dialdehyde and combinations of glutaric dialdehyde and epichlorohydrin. The solution is heated to a temperature between 10° C. to 100° C., preferably 80° C. to 95° C., to perform the cross-linking reaction. The reaction is carried out until cross-linking occurs to the point where a discernible increase in viscosity takes place and the gel is formed; usually a reaction time of 4 to 12 hours is required.

When glyoxal or glutaric dialdehyde is the cross-linking agent, it has been found desirable to add from 0.1 to 5 moles per 1,000 grams of lignin of epichlorohydrin to the reaction after about 4 to 6 hours have elapsed to assist in forming the insoluble gel. Lignins thus treated form water-insoluble reswellable gels with the amount of reswellability being greatest with glutaric dialdehyde and progressively somewhat lower with glyoxal and formaldehyde, respectively.

At this point during gel formation regardless of the reactants, some variation in the gel synthesis becomes possible. The reaction vessel can be opened and the gel allowed to partially dehydrate, and the reaction allowed to continue, or additional water can be added and the swollen volume of the gel increased several fold followed by further heating. These actions result in gels with varying degrees of swellability with the use of additional water producing a gel which displays an eight to eleven fold volume increase when the dried material is immersed in water. Dehydration increases the apparent cross-link density of the resultant gel. Typical gels produced in this manner have three to four fold volume increases when reswollen. After synthesis, the gels are broken up, washed with several volumes of water to remove any unreacted starting materials, and dried.

The differing surface chemical characteristics of the gels of this invention make them attractive as controlled release carriers for different pesticides. The low dry surface area and almost non-existent anhydrous pore structure of the aldehyde cross-linked gels enable them to accept and hold large quantities of liquid pesticides without rapid release of the toxicant once it has been incorporated into the gel. When the gel is dried, the loss of both area and apparent pore volume entraps much of the pesticide in the interior of the particles of the cross-linked lignin. Rapid release of the entrapped material does not take place because of the restricted diffusion of the pesticide through the carrier matrix whose apparent density has increased because of pore closure.

Inclusion of Pesticide

Pesticide inclusion is simply a matter of reswelling the gel in an aqueous solution of the pesticide or cross-linking the lignin in an aqueous solution of the pesticide. This, of course, presently limits this carrier to use primarily with water-soluble pesticides. The pesticide is included in an amount from 0.1:1 to 2:1 by weight ratio of pesticide to carrier. The final steps in composite formulations are drying, crushing and screening.

The pesticides that can be physically combined with the cross-linked lignin materials described hereinabove primarily include those that are water-soluble. Although to a much lesser extent, polar yet water-insoluble pesticides may be used if they are first solubilized in solvents, such as methanol, formamide, dimethyl formamide, dimethyl sulfoxide or other polar water-miscible solvents. The water-soluble pesticides will be released rapidly and over a shorter period of time than the water-insoluble pesticides. Some of the specific pesticides that may be employed are listed in the following table.

| Common Name | Proprietary Name | Chemical Description |
|---|---|---|
| 2,4-D amine or alkali salts | 2,4-D salt | 2,4-dichlorophenoxy-acetic acid salt |
| chloramben | AMIBEN | 3-amino-2,5-dichloro-benzoic acid (amine or salt) |
| dicamba | BANVEL | 3,6-dichloro-0-anioic acid (salt) |
| 2,4,5-T amine or alkali salts | | 2,4,5-Trichlorophenoxy acetic acid salt |
| 2,3,6-TBP | | Trichlorobenzoic acid salt |
| 2,4-D-B | | 4-(2,4-dichlorophenoxy) butyric acid (salt) |
| sodium or potassium azide | | $NaN_3$, $KN_3$ |

The composite formulations consisting of carrier and pesticide can be prepared by a variety of techniques as described above. It is preferable to slurry the solid carrier either swollen or non-swollen in liquid pesticides, applying heat and allowing the system to cool. Excess pesticide is removed by decantation or filtration. The pesticide may be dissolved in a non-swelling solvent, such as dichloromethane. The non-swollen carrier is heated, added to the solution, and the solvent evaporated. Heat may also be applied as above for solid agents. Composites may be prepared using technology currently in use for preparing conventional granular formulations which utilize clay or ground corn cob for carrier. That is, the heated carrier can be sprayed with a solution of the agent in a volatile solvent, such as dichloromethane.

While controlled release composites can be prepared as in the prior art using the chemically unmodified kraft lignin, certain advantages are realized with cross-linked lignin gels which are not immediately available with the unmodified lignins. High levels of pesticide loading with unmodified kraft lignin frequently result in composites which have been sufficiently plasticized to prevent grinding and milling to granular and powder formulations. The specific interactions between lignin carrier and pesticide which cause plasticization are reduced in the cross-linked lignins. Secondly, use of unmodified lignin requires dissolution of the lignin in either organic solvents or concentrated aqueous alkali. This requires additional processing by the pesticide handling operation and in the case of alkaline solutions produces an environment into which few organophosphate or carbamate-type pesticides can be introduced. Use of aqueous lignin solutions produces effluents often contaminated with pesticide. The gels already consist of preformed three-dimensional matrixes which after the initial preparation require no additional synthetic effort to produce a matrix.

Extended release of varying amounts of active pesticide can be controlled by the ratio of pesticide to lignin carrier. The amount of pesticide that is physically interspersed within the lignin gel is one of the factors which dictate the time which is needed for release of the pesticidal compound to the applicable site. The particular amount of cross-linking or processing conditions to form the lignin gels affects the release mechanism by virtue of the pore structure and cross-link density of the lignin gel. Thus, the amount of pesticide that is released over a given period of time can be controlled by selecting the process conditions for obtaining the cross-linked gels and the degree of loading of toxicant.

The sustained release compositions of this invention have numerous advantages to the ultimate user over other known pesticide compositions, these advantages including ease and handling solids as opposed to liquids, reduced toxicity to humans and other animal life, control of continuous release of active pesticide composites, lower risks of over-application, and fewer and more efficient applications. The exact dosage applied depends upon the release rate of the composition, vegetation or insect to be controlled, the duration of control desired, and the pesticide employed.

The practice of this invention is clearly illustrated by the following examples.

EXAMPLE 1

A sodium salt of kraft pine lignin having a concentration of about 20% solids was reacted with 5 moles of formaldehyde per 1,000 grams of lignin. The lignin solution at pH 12 is brought to 90° C. and the formaldehyde (as paraformaldehyde) added. Seven (7) hours are required at 90° C. for the cross-linking reaction to proceed to the point where a discernible increase in viscosity takes place. From this point, the viscosity continued to increase at an accelerated rate. Two (2) hours additional reaction produced a gel which will not flow when removed from the reaction vessel.

EXAMPLE 2

Lignin concentrations varying from 20%–25% were reacted with 5 moles of glyoxal per kilogram of lignin to cross-link. The lignin solutions at pH 12 were brought to 95° C., and the glyoxal as a 40% aqueous solution was added. Five (5) hours of reaction were required for a discernible increase in viscosity to occur. At this point, additional water and 0.5 mole of epichlorohydrin per 1,000 grams of lignin were added and heating continued for 2 additional hours. The materials were readily deformable thick black pastes.

EXAMPLE 3

Lignin at a concentration of about 25% and 5 moles of glutaric dialdehyde were cross-linked to form a gel. The lignin solution at pH 12 was brought to 95° C. and the glutaric dialdehyde added as a 25% aqueous solution. Five (5) to six (6) hours were required for a desirable increase in viscosity to occur. At that time, additional water and 0.5 mole of epichlorohydrin per 1,000 grams of lignin were added and heating at 95° C. was continued for 2 hours. The reaction vessel was opened and heated for an additional hour to partially dehydrate the gel.

EXAMPLE 4

Twenty (20) grams of dehydrated cross-linked lignin gel from Example 1 were slurried in 75 milliliters of water. When all of the water was absorbed, an additional 25 milliliters of water containing 0.0872 gram of the triethanol amine salt of 2,4-D herbicide were added. The swollen gel was heated at 100° C. until the water was removed. The gel containing the amine salt was then slurried in 50 milliliters of water containing enough HCl (0.975 milliliter of 0.012 N HCl) to convert 50% of the salt already in the gel to the acid form. The dual nature of the herbicide in the lignin gel produced the water-soluble amine salts of 2,4-D for quick release and initial biological control and slightly water-soluble 2,4-D acid for extended control.

EXAMPLE 5

In this example, a small field test was conducted using a lignin gel-2,4-D amine salt composite formulation. Test samples were prepared by mixing and blending 100 grams of dry soil with enough gel composite to achieve an application rate of $5.2 \times 10^{-3}$ grams 2,4-D anion per square foot. The gel contained 3% 2,4-D with 75% of the herbicide present as the triethanolamine salt and the remaining as the acid. A series of soil trays consisting of 16 compartments each 1 ft.$^2$ in area were used. In one tray, 12 compartments were treated with the 2,4-D controlled release material and 4 were covered with a fine screen. The second tray consisted of 12 control compartments with no herbicide and 4 covered controls.

The herbicide was applied as a 40×60 mesh granular at a rate of ½ pound per acre. Rye grass and Kentucky Bush bean seeds were immediately over planted in the trays. No planting was done on the control tray. Within three weeks, rye grass had sprouted in the treated tray. Rye was used as a simulant for grasses and grains which presently received 2,4-D treatment as a pre-emergent herbicide. No beans sprouted during the first four weeks. Thereafter, the herbicide treated trays were planted with beans at three-week intervals with no growth observed. Broadleaf weeds were observed to be growing in the untreated trays within five weeks of the initiation of the tests.

The weeds growing in the trays were counted twice during the test. After 18 weeks, the treated trays were found to average 6 weeds per ft.$^2$, while the untreated plots averaged 30. After 30 weeks, the treated trays averaged 1 weed per ft.$^2$, while the untreated average remained 30. Plots treated with ½-pound/acre 2,4-D as a 4-pound/gallon commercial formulation provided weed control for seven weeks.

Upon termination after 31 weeks, the untreated average was 1 broadleaf/ft.$^2$ and the untreated at 30. In this case, control was effective for 29 weeks and still effective; whereas, conventional formulations stopped working after seven weeks. Here is an indication of the same amount of agent doing the job for a much longer time or the same period of control provided by a considerably smaller amount of herbicide.

While the invention has been described and illustrated herein by references to various specific materials, procedures and examples, it is understood that the invention is not restricted to the particular material, combinations of material, and procedures selected for that purpose. Numerous variations of such details can be employed as will be appreciated by those skilled in the art.

What is claimed is:

1. A cross-linked lignin gel for use as a controlled release herbicide carrier comprising the reaction product of an aqueous solution of alkali lignin at a concentration of 10% to 40% weight by volume with from 1 to 10 moles of a cross-linking agent selected from the group consisting of formaldehyde, glyoxal, and glutaric dialdehyde reacted at a temperature between about 10° C. and 100° C. until a reversibly swellable gel is formed.

2. The lignin gel of claim 1 wherein said cross-linking agent is formaldehyde.

3. The lignin gel of claim 1 wherein said cross-linking agent is glutaric dialdehyde and from 0.1 to 5 moles per 1,000 grams of lignin of epichlorohydrin is added.

4. The lignin gel of claim 1 wherein said lignin is at a concentration from 20% to 25% and said reaction is carried out at about 80° C. to 95° C. for from 5 to 9 hours.

5. In a controlled release herbicide composition comprising a lignin carrier and a herbicide physically interspersed throughout at a weight ratio of 0.1:1 to 2:1 herbicide-to-lignin carrier which herbicide is released over an extended period of time under environmental conditions indigenous to agriculture, the improvement comprising the cross-linked, reversibly swellable alkali lignin gel of claim 1, and said controlled release composition being used in an amount containing an effective amount of herbicide.

* * * * *